United States Patent [19]

Almquist et al.

[11] Patent Number: 5,262,521

[45] Date of Patent: Nov. 16, 1993

[54] ISOLATED ATRIAL PEPTIDE-DEGRADING ENZYME AND NOVEL COMPOUNDS USEFUL AS INHIBITORS THEREOF

[75] Inventors: Ronald G. Almquist, Palo Alto; Lawrence Toll, Mountain View, both of Calif.

[73] Assignee: SRI International, Menlo Park, Calif.

[21] Appl. No.: 714,540

[22] Filed: Jun. 7, 1991

[51] Int. Cl.$^5$ .................................... A61K 37/02
[52] U.S. Cl. ........................ 530/327; 930/21
[58] Field of Search ............ 514/13, 14; 530/326, 530/327; 930/21

[56] References Cited

U.S. PATENT DOCUMENTS

| | | | |
|---|---|---|---|
| 4,716,147 | 12/1987 | Tjoeng et al. | 530/326 |
| 4,740,499 | 4/1988 | Olins | 514/13 |
| 4,816,443 | 3/1989 | Brady et al. | 530/326 |
| 4,952,561 | 8/1990 | Scolnick et al. | 514/14 |
| 5,057,603 | 10/1991 | Nutt et al. | 530/324 |

FOREIGN PATENT DOCUMENTS 8806596  9/1988  World Int. Prop. O. .

OTHER PUBLICATIONS

Dayhoff et al., Atlas of Protein Sequence and Structure, vol. 5 pp. 89–99 (1972).
M. G. Currie et al., *Science*, 221: 71–73 (1983).
M. G. Currie et al., *Science*, 223:67–69 (1984).
A. J. de Bold et al., *Life Science*, 28:89–94 (1981).
A. J. de Bold et al., *Science*, 230:767–770 (1985).
J. G. de Mey, *J. Pharmacol. Exp. Therap.*, 240 (3):937–943 (1986).
T. G. Flynn et al., *Biochem. Biophys. Res. Commun.*, 117:859–865 (1983).
R. Garcia, *Experientia*, 38:1071–73 (1982).
R. Garcia et al., *Biochem. Biophys. Res. Commun.*, 126:178–184 (1985).
D. M. Geller et al., *Biochem. Biophys. Res. Commun.*, 120(2): 333–338 (1984).
R. B. Harris et al., *Arch. Biochem. Biophys.*, 233:667–675 (1984).
R. B. Harris et al., *Peptides*, 6:393–396 (1985).
G. R. Johnson et al., *J. Biol. Chem.*, 264:11637–11642 (1989).
G. R. Johnson et al., *Biochem. Biophys. Res. Commun.*, 167:110–116 (1990).
K. Kangawa et al., *Biochem. Biophys. Res. Commun.*, 118:131–139 (1984).
K. Kangawa et al., *Biochem. Biophys. Res. Commun.*, 119:933–940 (1984).
K. Kangawa et al., *Biochem. Biophys. Res. Commun.*, 121: 585–591 (1984).
N. Katsube et al., *Biochem. Biophys. Res. Commun.*, 128:325–330 (1985).
J. A. Koehn et al., *J. Biol. Chem.*, 262:11623–11627 (1987).
P. Needleman et al., *Hypertension*, 7(2):469–482 (1985).
G. M. Olins et al., *Eur. J. Biochem.*, 170:431–434 (1987).
J. L. Sonnenberg et al., *Peptides*, 9:173–180 (1988).
S. R. Stephenson et al., *Biochemistry*, 243:183–187 (1987).
M. Sugiyama, *Biochem. Biophys. Res. Commun.*, 123(1):338–344 (1984).
L. Toll, *Biochem. Biophys. Res. Commun.*, 175:886–893 (1991).

*Primary Examiner*—Merrell C. Cashion, Jr.
*Assistant Examiner*—Bennett Celsa
*Attorney, Agent, or Firm*—Dianne E. Reed

[57] ABSTRACT

A novel atrial peptide-degrading enzyme (ADE) is provided in isolated, purified form. The enzyme has a molecular weight of approximately 160,000 Daltons as measured by gel filtration chromatography, and is effective to cleave atrial peptides such as APII, APIII and ANF. Also provided are novel compounds useful as inhibitors of the enzyme and thus useful as blood pressure lowering agents, pharmaceutical compositions containing the inhibitors, and methods of using the inhibitors.

5 Claims, 1 Drawing Sheet

FIG. 1

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear     ( i i ) MOLECULE TYPE: protein     ( x i ) SEQUENCE DESCRIPTION: SEQ ID NO:1:

```
Ser Leu Arg Arg Ser Ser Ala Gly Ala Asn
1               5                    10
```

( 2 ) INFORMATION FOR SEQ ID NO:2:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear     ( i i ) MOLECULE TYPE: protein     ( x i ) SEQUENCE DESCRIPTION: SEQ ID NO:2:

```
Ser Leu Arg Arg Ser Ser Ala Gly Ala Asn Ser Phe Arg Tyr
1               5                    10
```

( 2 ) INFORMATION FOR SEQ ID NO:3:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear     ( i i ) MOLECULE TYPE: protein     ( x i ) SEQUENCE DESCRIPTION: SEQ ID NO:3:

```
Ser Leu Arg Arg Ser Ser Ala Gly Ala Asn Cys Phe Arg Tyr
1               5                    10
```

( 2 ) INFORMATION FOR SEQ ID NO:4:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear     ( i i ) MOLECULE TYPE: protein     ( x i ) SEQUENCE DESCRIPTION: SEQ ID NO:4:

```
Ser Leu Arg Arg Ser Ser Ala Gly Ala Asn Cys Phe Arg
1               5                    10
```

( 2 ) INFORMATION FOR SEQ ID NO:5:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear     ( i i ) MOLECULE TYPE: protein     ( x i ) SEQUENCE DESCRIPTION: SEQ ID NO:5:

```
Leu Tyr Lys Lys Ile Ile Lys Lys Leu Leu Glu Ser
1               5                    10
```

( 2 ) INFORMATION FOR SEQ ID NO:6:

( i ) SEQUENCE CHARACTERISTICS:
    ( A ) LENGTH: 19 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:6:

```
Asn Leu Ala Lys Gly Lys Glu Glu Ser Leu Asp Ser Asp Leu Tyr Ala
1               5                   10                  15
Glu Leu Arg
```

( 2 ) INFORMATION FOR SEQ ID NO:7:

( i ) SEQUENCE CHARACTERISTICS:
    ( A ) LENGTH: 8 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:7:

```
Asp Val Asn Thr Asp Arg Pro Gly
1               5
```

( 2 ) INFORMATION FOR SEQ ID NO:8:

( i ) SEQUENCE CHARACTERISTICS:
    ( A ) LENGTH: 13 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:8:

```
Glu Leu Tyr Glu Asn Lys Pro Arg Arg Pro Tyr Ile Leu
1               5                   10
```

( 2 ) INFORMATION FOR SEQ ID NO:9:

( i ) SEQUENCE CHARACTERISTICS:
    ( A ) LENGTH: 10 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:9:

```
Glu His Trp Ser Tyr Gly Leu Arg Pro Gly
1               5                   10
```

( 2 ) INFORMATION FOR SEQ ID NO:10:

( i ) SEQUENCE CHARACTERISTICS:
    ( A ) LENGTH: 5 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:10:

```
Asn Ser Phe Arg Tyr
1               5
```

(2) INFORMATION FOR SEQ ID NO:11:

(i) SEQUENCE CHARACTERISTICS:
        (A) LENGTH: 4 amino acids
        (B) TYPE: amino acid
        (C) STRANDEDNESS: single
        (D) TOPOLOGY: linear     (ii) MOLECULE TYPE: protein     (xi) SEQUENCE DESCRIPTION: SEQ ID NO:11:

Asn Ser Phe Arg
    1

(2) INFORMATION FOR SEQ ID NO:12:

(i) SEQUENCE CHARACTERISTICS:
        (A) LENGTH: 4 amino acids
        (B) TYPE: amino acid
        (C) STRANDEDNESS: single
        (D) TOPOLOGY: linear     (ii) MOLECULE TYPE: protein     (xi) SEQUENCE DESCRIPTION: SEQ ID NO:12:

Ser Phe Arg Tyr
    1

(2) INFORMATION FOR SEQ ID NO:13:

(i) SEQUENCE CHARACTERISTICS:
        (A) LENGTH: 4 amino acids
        (B) TYPE: amino acid
        (C) STRANDEDNESS: single
        (D) TOPOLOGY: linear     (ii) MOLECULE TYPE: protein     (xi) SEQUENCE DESCRIPTION: SEQ ID NO:13:

Cys Phe Arg Tyr
    1

ISOLATED ATRIAL PEPTIDE-DEGRADING ENZYME AND NOVEL COMPOUNDS USEFUL AS INHIBITORS THEREOF

FIELD OF THE INVENTION

This invention relates generally to a newly isolated and characterized atrial peptide-degrading enzyme ("ADE") and to novel compounds that have been found to be inhibitors thereof. The invention also encompasses pharmaceutical compositions containing the novel inhibitors and methods of using the inhibitors to inhibit the enzymatic activity of ADE.

BACKGROUND OF THE INVENTION

Most multi-cellular organisms are organized into tissues and organs which perform specialized functions, and the "circulatory" system has evolved to transport and circulate materials between them. In higher animals, including mammals, the circulatory system is closed, in order to improve the efficiency of transport. The flow of blood fluid through this closed cardiovascular system requires that the fluid be maintained under pressure and that the pressure be regulated in some way. The regulation of systemic arterial blood pressure requires a complex interaction of numerous factors including, for example, fluid volume and vascular elasticity.

The maintenance of normal extracellular fluid volume depends primarily on the excretion of sodium (natriuresis) and water (diuresis) by the kidneys. This is determined by both the rate at which plasma is filtered at the glomerulus and the degree to which sodium is actively reabsorbed along the renal tubule. The latter process is in part regulated by the adrenal steroid hormone aldosterone. However, it has now been established that, in addition to GFR and aldosterone, there are additional "factors" which also regulate sodium reabsorption and thus the conditions present in the circulatory system.

The report by debold and coworkers in 1981 (A. J. debold et al., *Life Sci.* 28:89-94 (1981)) that intravenous injection of an atrial myocardial extract into rats caused a rapid and potent natriuretic response set off a detailed search over the next several years for the sequences of peptides that were responsible for this circulatory system activity. The results of this search are summarized by debold in *Science* 230:767-770 (1985), in which a report is presented on a series of atrial peptides and their enzymatic cleavage products that range in length from 21 to 152 amino acids. Also in the aforementioned reference is a description of the circulating form of an "atrial natriuretic factor" ("ANF") as a carboxy terminal 28 amino acid fragment of the 126 amino acid α-ANF that is found stored in the atrial granules.

Further studies on various circulating forms of ANF indicated that three additional peptides were readily found in serum. These peptides, termed atriopeptin I ("API"), atriopeptin II ("APII") and atriopeptin III ("APIII"), were found to have various activities and potencies in both in vitro and in vivo studies (see, e.g., K. F. Siegel et al., *Biochem. Biophys. Res. Commun.* 120:333-338 (1984); and M. L. Michener et al., *Hypertension* 7:469-482 (1985)). Moreover, the significantly reduced potency of API in a variety of systems, compared to APII and APIII, indicates that processing to API may be an important mechanism of hormone activation (G. Thibault, *Biochem. Biophys. Res. Commun.* 123:338-344 (1984); R. G. Garcia, *Biochem. Biophys. Res. Commun.* 126:178-184 (1985); J. G. De Mey, *J. Pharmacol. Exp. Therap.* 240:937-943 (1986)).

After the initial reports describing the various peptides, it became clear that inhibition of a specific cleavage enzyme could have medical applications due to its ability to increase the lifetime of circulating atrial peptides. One enzyme in particular, neutral endopeptidase 24.11 (also known as "enkephalinase") has received considerable attention in light of its presence in kidney brush border membranes, and its ability to cleave atrial peptides between the Cys-Phe linkage present inside the disulfide ring (G. M. Olins et al., *Eur. J. Biochem.* 170:431-434 (1987); S. R. Stephenson et al., *Biochemistry* 243:183-187 (1987); J. L. Sonnenberg et al., *Peptides* 9:173-180 (1988)). In examining the kidney as a potential source for selective degrading enzymes, with particular interest in the conversion of ANF, APII or APIII to API, the present inventors discovered a new atrial peptide-degrading enzyme isolated from bovine kidney which cleaves ANF, APII and APIII between the carboxy terminally located Ser and Phe residues. Thus, the present invention is directed in part to this newly discovered enzyme in isolated, purified form. This enzyme is referred to herein as atrial peptide-degrading enzyme, or "ADE".

The present invention is also directed to a class of novel, synthetic compounds which have been found by the inventors herein to be useful as inhibitors of ADE and are thus believed to have utility as circulatory system moderators and thus as blood pressure lowering agents. These compounds are oligopeptides or polypeptides which are characterized by a "core" of 13 or 14 amino acid residues as will be described below.

RELATED ART

In addition to the publications mentioned in the preceding sections, the following references relate to one or more aspects of the present invention:

M. G. Currie et al., Science, 221:71-73 (1982);

M. G. Currie et al., Science, 223:67-69 (1984);

T. G. Flynn et al., Biochem. Biophys. Res. Commun., 117:859-865 (1983);

R. Garcia, *Experientia*, 38:1071-73 (1982);

R. Garcia et al., Biochem. Biophys. Res. Commun., 126:178-184 (1985);

R. B. Harris et al., *Arch. Biochem. Biophys.*, 667-675 (1984);

R. B. Harris et al., *Peptides*, 6:393-396 (1985);

G. R. Johnson et al., *J. Biol. Chem.*, 264:11637-11642 (1989);

G. R. Johnson et al., *Biochem. Biophys. Res. Commun.*, 167:110-116 (1990);

K. Kangawa et al., *Biochem. Biophys. Res. Commun.*, 118:131-139 (1984);

K. Kangawa et al., *Biochem. Biophys. Res. Commun.*, 119:933-940 (1984);

K. Kangawa et al., Biochem. Biophys. Res. Commun., 121:585-591 (1984);

N. Katsube et al., Biochem. Biophys. Res. Commun., 128:325-330 (1985);

J. A. Koehn et al., *J. Biol. Chem.*, 262:11623-11627 (1987); and

L. Toll, *Biochem. Biophys. Res. Commun.*, 175:886-893 (1991).

SUMMARY OF THE INVENTION

It is a primary object of the invention to provide a newly characterized enzyme which has atrial peptide-degrading activity, in isolated, substantially pure form.

It is still another object of the invention to provide novel compounds useful as inhibitors of the aforementioned enzyme and which may thus be useful as blood pressure lowering agents.

It is still a further object of the invention to provide pharmaceutical compositions containing the aforementioned inhibitor compounds.

It is still another object of the invention to provide methods of using the novel compounds to inhibit ADE activity.

Additional objects, advantages and novel features of the invention will be set forth in part in the description which follows, and in part will become apparent to those skilled in the art upon examination of the following, or may be learned by practice of the invention.

In one aspect, then, the invention provides an isolated, purified atrial peptide-degrading enzyme (ADE) having a molecular weight of approximately 160,000 Daltons as measured by gel filtration chromatography, and which is effective to cleave the atrial peptides APII, APIII and ANF between the Ser-Phe linkage at the carboxy terminus of the peptides.

In another aspect, the invention provides a novel class of compounds which are inhibitors of ADE activity. The compounds are peptides which include the amino acid sequence (A)

(A) $AA_1$-$AA_2$-$AA_3$-$AA_4$-$AA_5$-$AA_6$-$AA_7$-$AA_8$-$AA_9$-$AA_{10}$-$AA_{11}$-$AA_{12}$-X wherein:

$AA_1$, $AA_5$, $AA_6$, $AA_{10}$ and $AA_{11}$ are independently selected from the group consisting of neutral, polar amino acids;

$AA_2$, $AA_7$, $AA_8$ and $AA_9$ are independently selected from the group consisting of neutral, non-polar aliphatic amino acids;

$AA_3$ and $AA_4$ are independently selected from the group consisting of basic amino acids;

$AA_{12}$ is an aromatic amino acid; and

X is -$AA_{13}$ or -$AA_{13}$-$AA_{14}$ wherein $AA_{13}$ is a basic, aliphatic amino acid and $AA_{14}$ is any neutral or basic, polar or nonpolar, aliphatic or aromatic amino acid.

These compounds are useful as blood pressure lowering agents.

In still another aspect of the invention, pharmaceutical compositions are provided which contain one or more of the aforementioned peptide inhibitors in combination with an inert, pharmaceutically acceptable carrier. The invention also encompasses methods of using the compositions in pharmaceutically effective dosage regimens to lower blood pressure in mammals.

DETAILED DESCRIPTION OF THE INVENTION

Definitions and Abbreviations

Before describing the present compounds, compositions and methods of the invention in detail, it is to be understood that this invention is not limited to the particular isolation or purification techniques described, or to particular reagents used to prepare the novel compounds and compositions, or the like, as such may vary. It is also to be understood that the terminology used herein is for the purpose of describing particular embodiments only, and is not intended to be limiting.

It must be noted that, as used in this specification and the appended claims, the singular forms "a", "an" and "the" include plural referents unless the content clearly dictates otherwise. Thus, for example, reference to a method of using "an ADE inhibitor compound" includes a method of using two or more ADE inhibitor compounds, reference to administration of "a pharmaceutical composition" includes reference to administration of one or more such compositions, and the like.

In describing and claiming the present invention, the following nomenclature will be used in accordance with the definitions set out below.

Amino acid residues can be generally subclassified as follows.

Basic: The residue has a positive charge due to association with a hydrogen ion at physiological pH and the residue is attracted by aqueous solution so as to seek the surface positions in the conformation of a peptide in which it is contained when the peptide is in aqueous medium at physiological pH.

Neutral, polar: The residues are not charged at physiological pH, but are attracted by aqueous solution. These residues are also designated "hydrophilic".

Neutral, nonpolar: The residues are not charged at physiological pH, and are repelled by aqueous solution. These residues are also designated "hydrophobic".

The terms "aliphatic", "aromatic" and "nonaromatic" are used according to the conventional definitions of the terms.

It is understood, of course, that in a statistical collection of individual residue molecules some molecules will be charged, and some not, and there will be an attraction for or repulsion from an aqueous medium to a greater or lesser extent. To fit the definition of "charged," a significant percentage (at least approximately 25%) of the individual molecules are charged at physiological pH. The degree of attraction or repulsion required for classification as polar or nonpolar is arbitrary, and, therefore, amino acids specifically contemplated by the invention have been specifically classified as one or the other. Most amino acids not specifically named can be classified on the basis of known behavior.

For the naturally occurring protein amino acids, subclassification according to the foregoing scheme is as follows:

Basic: Arginine, lysine, histidine;

Neutral, polar: Serine, threonine, cysteine, methionine, asparagine, glutamine;

Neutral, nonpolar: Glycine, alanine, valine, leucine and isoleucine;

Aromatic: Phenylalanine, tyrosine and tryptophan.

The nomenclature used to describe the ADE inhibitor compounds of the present invention follows the conventional practice wherein the amino group is assumed to the left and the carboxy group to the right of each amino acid in the peptide. In the formulae representing selected specific embodiments of the present invention, the amino- and carboxy-terminal groups, although often not specifically shown, will be understood to be in the form they would assume at physiological pH values unless otherwise specified. Thus, the N-terminal H+ and C-terminal —O− at physiological pH are understood to be present though not necessarily specified and shown, either in specific examples or in generic formulas. The invention also encompasses compounds wherein one or more of the amino acids in the polypeptide chain are conventionally modified, and compounds wherein the N-terminus is acylated and/or the C-terminus is modified so that the normally present —OH moiety is converted to an —NH₂ or —OR group (wherein R is alkyl or aryl). Compounds wherein the C-terminal —OH has been so modified will generally be designated herein as ". . . —NH₂," ". . . —OR," etc.

In the peptides shown, each encoded residue will sometimes herein be represented by the conventional abbreviations, corresponding to the trivial name of the amino acid, in accordance with the following convention list:

| Amino Acid | Three-letter Symbol |
|---|---|
| Alanine | Ala |
| Arginine | Arg |
| Asparagine | Asn |
| Aspartic acid | Asp |
| Cysteine | Cys |
| Glutamine | Gln |
| Glutamic acid | Glu |
| Glycine | Gly |
| Histidine | His |
| Isoleucine | Ile |
| Leucine | Leu |
| Lysine | Lys |
| Methionine | Met |
| Phenylalanine | Phe |
| Proline | Pro |
| Serine | Ser |
| Threonine | Thr |
| Tryptophan | Trp |
| Tyrosine | Tyr |
| Valine | Val |

In the specific peptides shown in the present application, the L-form of any amino acid residue having an optical isomer is intended unless otherwise expressly indicated as the D-form.

Other abbreviations used herein are as follows:

| Abbreviation | Chemical or Group |
|---|---|
| Boc | t-butoxycarbonyl |
| DCC | dicyclohexylcarbodiimide |
| DCM | dichloromethane |
| DIEA | diisopropylethylamine |
| E64 | trans-Epoxysuccinyl-L-leucylamido-(4-guanidino)butane |
| EDTA | Ethylenediamine tetraacetic acid |
| HOBt | 1-hydroxybenzotriazole |
| NEM | N-ethylmaleimide |
| PMSF | Phenylmethylsulfonyl fluoride |
| TFA | trifluoroacetic acid |

Purified ADE

In a first embodiment, the invention is directed to a newly isolated and characterized enzyme which has atrial peptide-degrading activity. Isolation and purification of the enzyme is described in detail in Example 1 herein. Briefly, the enzyme is isolated from fresh bovine kidney (as described in Example 1, part (b)) and purified via one or more chromatographic steps. Preferably, ion exchange chromatography is carried out first, followed by chromatographic purification on a hydroxylapatite column, which is in turn followed by HPLC and a size exclusion step. The isolated enzyme so obtained ("ADE") is in substantially pure form; the term "substantially pure" as used herein is intended to mean that degree of purity obtained upon carrying out the various steps summarized above and exemplified in Example 1, part (b).

ADE has been found by the inventors herein to cleave a variety of substrates. In particular, and as shown in Example 1, ADE prefers atrial peptides as substrates and cleaves them at the Ser-Phe linkage near the carboxy terminus to give API analogs or the amino-terminally extended form of API when ANF is used as substrate.

The molecular weight of ADE—approximately 160,000 Daltons as determined by gel filtration chromatography—and the inhibitor profile (determined in Example 1) suggest that this enzyme might be similar to that described by G. R. Johnson et al. (1989) and (1990), cited supra. Both proteins are inhibited by metal chelators as well as by the thiol reagent NEK. This suggests that a crucial cysteine residue, as well as a chelated metal, is necessary for enzymatic activity.

While the physiological significance of this soluble renal enzyme is not entirely clear, the high affinity for various atrial peptides as well as the specificity of its enzymatic activity (Table 2 of Example 1) indicate that ADE does degrade natural atrial peptides in vivo and thus has a role in the processing and/or clearance of atrial peptides.

The ADE Inhibitors

In another embodiment of the invention, novel polypeptide compounds are provided which serve as inhibitors of ADE activity and are thus useful as blood pressure lowering agents. These compounds, as noted above, may be generically represented by the formula $AA_1$-$AA_2$-$AA_3$-$AA_4$-$AA_5$-$AA_6$-$AA_7$-$AA_8$-$AA_9$-$AA_{10}$-$AA_{11}$-$AA_{12}$-X where $AA_1$, $AA_2$, $AA_3$, $AA_4$, $AA_5$, $AA_6$, $AA_7$, $AA_8$, $AA_9$, $AA_{10}$, $AA_{11}$, $AA_{12}$, and X may be generally described as outlined above.

Preferred inhibitor compounds within this group are wherein:

$AA_1$, $AA_5$, $AA_6$, $AA_{10}$, and $AA_{11}$ are independently selected from the group consisting of serine, threonine, cysteine, methionine, asparagine and glutamine;

$AA_2$, $AA_7$, $AA_8$ and $AA_9$ are independently selected from the group consisting of glycine, alanine, valine, leucine and isoleucine;

$AA_3$ and $AA_4$ are independently selected from the group consisting of arginine, lysine and histidine;

$AA_{12}$ is selected from the group consisting of phenylalanine, tyrosine and tryptophan; and X is -$AA_{13}$-$AA_{14}$ where $AA_{13}$ is selected from the group consisting of arginine, lysine and histidine and $AA_{14}$ is tyrosine.

Also preferred are compounds wherein X is -$AA_{13}$ where $AA_{13}$ is selected from the group consisting of arginine, lysine and histidine.

Particularly preferred inhibitor compounds within this group have the formula

Ser-Leu-Arg-Arg-Ser-Ser-DAla-Gly-DAla-Asn-$AA_{11}$-$AA_{12}$-X (SEQ ID NO:1).

Examples of such particularly preferred inhibitor compounds are tetradecapeptides having an amino acid sequence selected from the following sequences (I), (II), (III), (IV), (V) and (VI):

(I) Ser-Leu-Arg-Arg-Ser-Ser-DAla-Gly-DAla-Asn-Ser-Phe-Arg-Tyr-NH$_2$ (SEQ ID NO:2);

(II) Ser-Leu-Arg-Arg-Ser-Ser-DAla-Gly-DAla-Asn-Ser-DPhe-Arg-Tyr-NH$_2$ (SEQ ID NO:2);

(III) Ser-Leu-Arg-Arg-Ser-Ser-DAla-Gly-DAla-Asn-DSer-Phe-Arg-Tyr-NH$_2$ (SEQ ID NO:2);

(IV) Ser-Leu-Arg-Arg-Ser-Ser-DAla-Gly-DAla-Asn-Cys-Phe-Arg-Tyr-NH$_2$ (SEQ ID NO:3);

(V) Ser-Leu-Arg-Arg-Ser-Ser-DAla-GAy-DAla-Asn-Cys-DPhe-Arg-Tyr-NH$_2$ (SEQ ID NO:3);

(VI) Ser-Leu-Arg-Arg-Ser-Ser-DAla-Gly-DAla-Asn-Cys-DPhe-Arg-NH$_2$ (SEQ ID NO:4);

It will be appreciated by those of skill in the art that the foregoing are presented merely as preferred compounds which are representative of possible substitution patterns at the various amino acid positions. The structures designated as "preferred" are not intended to place limitations on possible amino acid substitutions. Also, although the "particularly preferred" structures (I) through (IV) are tetradecapeptides, inhibitor compounds containing the amino acid sequence (A) may be polypeptides containing as many as 150 or 160 amino acid residues.

SYNTHESIS OF THE ADE INHIBITOR COMPOUNDS

The polypeptides of the present invention may be synthesized by any techniques that are known to those skilled in the peptide art. An excellent summary of the many techniques so available may be found in J. M. Stewart and J. D. Young, *Solid Phase Peptide Synthesis*, 2nd Ed., Pierce Chemical Co., Rockford, Ill. (1984), and J. Meienhofer, *Hormonal Proteins and Pentides*, vol. 2, p. 46, New York: Academic Press, 1973, for solid phase peptide synthesis, and E. Schroder and K. Lubke, *The Pentides*, vol. 1, New York: Academic Press, 1965, for classical solution phase synthesis.

In general, these methods comprise the sequential addition of one or more amino acids or suitably protected amino acids to a growing peptide chain. Normally, either the amino or carboxyl group of the first amino acid is protected by a suitable protecting group. The protected or derivatized amino acid can then be either attached to an inert solid support or utilized in solution by adding the next amino acid in the sequence having the complementary (amino or carboxyl) group suitably protected, under conditions suitable for forming the amide linkage. The protecting group is then removed from this newly added amino acid residue and the next amino acid (suitable protected) is then added, and so forth. After all the desired amino acids have been linked in proper sequence, any remaining protecting groups (and any solid support) are removed sequentially or concurrently, to afford the final polypeptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide.

The preferred method for peptide synthesis for use herein involves synthesizing the peptide on a solid phase support. Typical solid supports are generally classified as cross-linked polymeric supports. These can include divinylbenzene cross-linked styrene-based polymers, for example, divinylbenzene-hydroxymethyl styrene copolymers, divinylbenzene-chloromethylstyrene copolymers, and divinylbenzene-benzhydrylaminopolystyrene copolymers. The last of these materials is described by P. G. Pietta et al. in *Chem. Commun.* 160 (1970), and offers the advantage of directly introducing the terminal amide function into the peptide chain, which function is retained by the chain when the chain is cleaved from the support.

Synthesis may use manual techniques or may be carried out-automatically, e.g., using an Applied BioSystems 430A Peptide Synthesizer (Foster City, California) or a Biosearch SAM II automatic peptide synthesizer (Biosearch, Inc., San Rafael, California).

PHARMACEUTICAL COMPOSITIONS, ADMINISTRATION AND USE

The aforementioned inhibitor compounds of the invention, as noted above, are useful as blood pressure lowering agents. Thus, these compounds, and compositions containing them, can find use as therapeutic agents to lower blood pressure in mammals.

In a preferred embodiment, then, the present inhibitor compounds are used within the context of a dosing regimen effective to treat high blood pressure. The compounds may be used alone, or in combination with one or more other compounds, e.g., ANF (see Example 3 and Tables 11 and 12).

A number of suitable dosing regimens have been developed for the administration of ADE inhibitors to treat hypertension, and are well-known in the art. Total daily dose administered to an individual in single or divided doses may be, for example, from about 1–100 mg/kg body weight and more usually 1–10 mg/kb. The specific dose level for any particular patient, however, will of course be dependent on the subject being treated, i.e., on the subject's age, body weight, general health, sex, diet, time of administration, route of administration, rate of excretion, severity of the particular disease undergoing therapy, and the like, as well as on the activity of the particular compound administered.

Administration of the active compounds described herein can be via any of the accepted modes of administration of therapeutic agents. These methods include oral, parenteral, intravenous, transdermal, subcutaneous, pulmonary, intranasal, rectal and other systemic modes. For those compounds which are orally active, oral administration is preferred. For other compounds, administration in the form of a long-acting injectable composition is preferred.

Depending on the intended mode of administration, the compositions may be in the form of solid, semi-solid or liquid dosage forms, such as, for example, suppositories, liquids, suspensions, or the like, preferably in unit dosage forms suitable for single administration of precise dosages. The compositions will preferably include a conventional pharmaceutical vehicle or excipient and one or more of the present ADE inhibitor compounds, and, in addition, may include other medicinal agents, pharmaceutical agents, carriers, adjuvants, diluents, etc.

For solid compositions, conventional nontoxic solids include, for example, pharmaceutical grades of mannitol, lactose, starch, magnesium stearate, sodium saccharin, talc, cellulose, glucose, sucrose, magnesium carbonate, and the like may be used. The active compound as defined above may be formulated as suppositories using, for example, a polyalkylene glycol, as the carrier.

Liquid pharmaceutically administrable compositions can, for example, be prepared by dissolving, dispersing, etc. an active compound as defined above and optional pharmaceutical adjuvants in an excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc.

Controlled release formulations, i.e., formulations in which drug is released in a controlled manner over a prolonged period of time, may be prepared to administer the active compounds of the invention. Such formulations are made with bioerodible polymers such as poly(lactic acid), poly(ortho esters), poly(ortho carbonates), or the like, or with other polymers which contain labile linkages which undergo cleavage at physiologic conditions. See, e.g., Choi et al. U.S. Pat. No. 4,093,709, Choi et al. U.S. Pat. No. 4,131,648, Heller et al. U.S. Pat. No. 4,304,767, Heller et al. U.S. Pat. No. 4,898,928, Heller et al. U.S. Pat. No. 4,946,931 and Heller et al. U.S. Pat. No. 4,957,998.

Actual method of preparing such dosage forms are known, or will be apparent, to those skilled in this art; for example, see *Remington's Pharmaceutical Sciences*, Mack Publishing Company, Easton, Pennsylvania, 15th Edition, 1975. The composition or formulation to be administered will, in any event, for purposes of treating high blood pressure, contain an effective amount of the desired ADE inhibitor, i.e., an amount effective to achieve the desired therapeutic effect in the subject being treated.

Parenteral administration, if used, is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of nontoxic auxiliary substances such as wetting or emulsifying-agents, pH buffering agents and the like, such as, for example, sodium acetate, sorbitan monolaurate, triethanolamine oleate, etc. A more recently revised approach for parenteral administration employs the implantation of a slow-release or sustained-release system, such that a constant level of dosage is maintained.

The following examples are intended to provide those of ordinary skill in the art with a complete disclosure and description of how to make the novel compounds of the invention, and are not intended to limit the scope of what the inventor regards as his invention in any way. Efforts have been made to insure accuracy in respect to numbers used (e.g., amounts, temperatures, etc.), but some experimental error and deviation should, of course, be allowed for. Unless indicated otherwise, parts are parts by weight, temperatures are in degrees centigrade, and pressure is at or near atmospheric.

EXAMPLES

Example 1

Isolation and Purification of ADE (a.) Materials and Methods: Rat atriopeptin I (rAPI), rat atriopeptin II (rAPII), their amino terminally acetylated derivatives and carboxy terminal fragments were prepared by solid phase synthesis on a Beckman 990C peptide synthesizer starting with commercially available t-Boc amino acid substituted Merrifield resin (Peninsula Labs, Belmont, Calif.). After amino acid assembly the resulting peptides were cleaved from the resin using HF +10% anisole, and the crude peptides were purified by preparative C HPLC using acetonitrile-water-0.1% TFA gradients on a sephadex LH-20 column, eluting with 0.1% aqueous acetic acid. Purity of all peptides was >95% as evaluated by $C_{18}$ HPLC analysis. Rat API and APII coeluted on $C_{18}$ HPLC with commercial samples (Bachem Inc., Torrance, Calif.) of these same peptides. Acetylated rAPI ("AcAPI") and rAPII ("AcAPII") were analyzed by 90 MHz NMR and for amino acid composition (Protein Structure Lab, Univ. of Cal., Davis, Calif.) and gave acceptable (±10%) results. Rat atriopeptin III (rAPIII) was purchased from Bachem Inc., Torrance, Calif.

BocAsnSerPhe-OCH$_3$ was prepared by stepwise coupling of succinate esters of BocSer and BocAsn to Phe—OCH$_3$. NMR (90 MHz) and $C_{18}$ HPLC confirmed structure and >95% purity, respectively.

All of the standard inhibitors listed in Table 4 were purchased from Sigma, except for captopril which was the generous gift of Squibb Pharmaceutical Co.

(b.) Enzyme Isolation Procedure: The cortex was removed from fresh bovine kidney and washed in 1 L each of ice-cold 0.9% Nacl and water. A 200-g portion of the tissue was then suspended in 400 mL of cold, 25 mM Hepes, pH 8. The suspension was homogenized three times in a one-speed blender for 30 sec, with 15-sec pauses, in a 4° C. room. The homogenate was then centrifuged at 8000×g for 20 min and the resulting supernatant was centrifuged at 54,500×g for 90 min. This high-speed supernatant was the soluble fraction containing the APII degrading enzyme.

The first purification step was ion-exchange chromatography on DE-53 cellulose (Whatman). First a 2.5×80-cm column of DE-53 cellulose was equilibrated with 25 mM Hepes, pH 8. Next, up to 300 mL of the high-speed supernatant was pumped onto the column at 1.5 mi/min. The column was then washed overnight with 25 mM Hepes, pH 8, at the same flow rate and the run-off was collected in one flask. During the wash, absorbance at 280 nm ("$A_{280}$") was monitored, which returned to near starting levels before elution was initiated. After sufficient washing, the column was eluted at 1.5 mi/min with 2 L of a 0–300 mm linear gradient of KCl in the Hepes buffer. Fractions (15 mi) were collected and monitored at $A_{280}$.

Fractions containing enzymatic activity were determined by the following method. First, 10 μL (0.6 μg/μL) of AcAPII (final concentration, 50 μM) containing 200 μM bestatin was mixed with 20 μL of H$_2$O and 20 μL of the appropriate column fraction. Samples were incubated at 37° C. for 60 min, then placed in a boiling water bath for 3 min. Samples were spun in a microfuge for about 1 min and 40 μL of the supernatant was transferred to HPLC assay vials. A 15 μL portion of the sample to be assayed was injected onto a Vydac $C_{18}$ HPLC column (TP 21854) and eluted with 22% acetonitrile in H$_2$O containing 0.1% trifluoroacetic acid. Enzymatic activity of fractions was quantitated by measuring the production of AcAPI. Protein was measured by the method of Lowry et al., *J. Biol. Chem*, 193:265–275 (1951).

The enzymatically active fractions were pooled and dialyzed overnight in 4 L of 12 mM K$_2$HPO$_4$, pH 7.6.

Then 100 mL of the dialyzed pool was pumped onto a 2.5×40 cm column of hydroxylapatite (BioRad) preequilibrated with the dialysis buffer. The run-off was collected in one flask. The column was washed with approximately 250 mL of 12 mM $K_2HPO_4$, pH 7.6 and the flow-through was collected in one flask. The $A_{280}$ was monitored until readings started to return to baseline. Finally, the column was eluted at 1 mL/min with 500 mL of a 12-500 mM linear gradient of $K_2HPO$ pH 7.6. Fractions (10 mL) were collected and their effect on AcAPII was assayed by the HPLC method described above.

Enzymatically active fractions from the hydroxylapatite column were pooled and concentrated tenfold using an ultrafiltration membrane with a molecular weight cut-off of 10,000. The concentrated sample was dialyzed overnight in 1 L of 10 mM potassium phosphate buffer, pH 7.5. Then 1.5 mL of the dialyzed concentrate was injected onto a 4.6×250 mm Rainin Dynamax (300 A AX) HPLC anion-exchange column. The column was eluted at 1 mL/min, with a 40 min, 10-300 mM linear gradient of $KHPO_4$ buffer, pH 7.5. Fractions (1 mL) were collected and assayed for AcAPII activity as described above.

Figure 1:
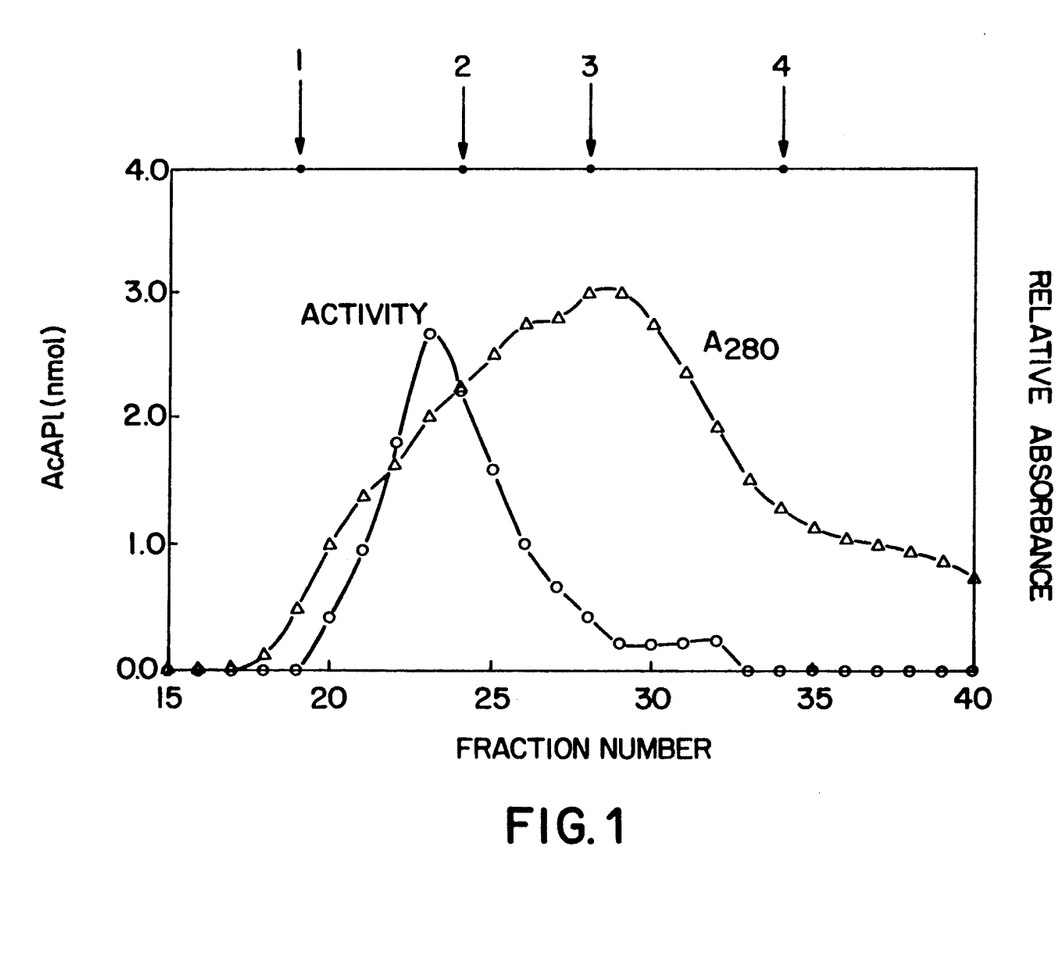
FIG. 1 graphically represents enzymatic activity from fractions containing ADE after elution from a Sephacryl S-200 size-exclusion chromatographic column (as described in Example 1, part (c).

Some of the Dynamax-purified material was chromatographed on a Sephacryl S-200 size-exclusion column (BioRad) eluting with 100 mM $K_2HPO_4$ (adjusted to pH 7.5 with HCl). Fractions (10 mL) were collected and their effect on AcAPII was assayed by the HPLC method described above. FIG. 1 shows that the enzyme activity from this column eluted in a symmetrical peak during the early stages of protein elution, slightly before aldolase, a standard protein with a molecular weight of approximately 158,000 Daltons.

(c.) ADE Substrate and Inhibitor Studies: To study substrate selectivity of the atrial peptide-degrading enzyme, the pooled fractions from the Dynamax HPLC ion exchange, or Sephacryl S-200 columns, were incubated with 50 μM synthetic substrate and incubated at 37° C. for one or two hours. At the appropriate time, the samples were boiled, centrifuged and analyzed on the Vydac column as described above. The amount of substrate present after the incubation, as determined by integration of the HPLC peak, was compared with the initial substrate level.

To determine the extent of inhibition of enzymatic activity, the enzyme preparation eluted from the Dynamax column was incubated with 50 μM AcAPII plus the desired inhibitor for 1 hour at 37° C., at which time samples were prepared for injection into the HPLC, as described above. The concentration of enzyme and AcAPII were chosen so that approximately 80% of the AcAPII was degraded in the absence of inhibitor. The production of AcAPI was determined by integration of the AcI peak, and percent inhibition by the inhibitors was calculated.

Table 1 shows the purification and recovery of enzymatic activity afforded by the four steps of column chromatography. For the determination of enzymatic activity, we used the production of AcAPI in 1 h at 37° C. Activity could not be measured in the original homogenate or in the supernatant from the initial centrifugation due to the presence of additional protease activity in these fractions (in these fractions, AcAPI was degraded by other peptidases almost as fast as it was produced by the atrial peptide-degrading enzyme (ADE), so by measuring AcAPI production the true amount of ADE activity present would be severely underestimated; conversely, by measuring AcAPII degradation, ADE activity would be overestimated). In the later steps of purification, there was an apparent increase in enzymatic activity after hydroxylapatite chromatography. These four steps provided approximately 50-fold purification (while the total degree of purification from the initial homogenate was obviously much greater).

TABLE 1

Purification of Atrial Peptide-degrading Enzyme

| Sample | AcAPI (μmol/h) | Total Protein (mg) | Specific Activity (nmol/min/mg) | % Recovery Activity | % Recovery Protein |
|---|---|---|---|---|---|
| DE-53 | 27.8 | 478.0 | 1.0 | 100 | 100.0 |
| Hydroxylapatite | 13.0 | 121.0 | 1.8 | 47 | 25.0 |
| Dynamax | 24.6 | 39.2 | 10.5 | 88 | 8.2 |
| S-200 | 12.3 | 3.9 | 52.4 | 44 | 0.8 |

For studies on enzymatic and inhibitor activity, the pooled fractions from the Dynamax column were used. This fraction had only one apparent activity on AcAPII; i.e., it cleaved AcAPII to AcAPI with no further degradation of the product AcAPI.

(d.) Substrate specificity: The ability of ADE to cleave a variety of substrates was examined. Table 2 shows the ability of ADE to cleave atrial peptides and other selected peptides of 8 to 19 amino acids. Atrial peptides are the preferred substrates, and are cleaved by ADE at the Ser-Phe linkage near the carboxy terminus to give API analogs or the amino-terminally extended form of API when ANF is used as substrate. Connective Tissue Activating Peptide (C-TAP) 1-19 was also found to be a good substrate for ADE.

TABLE 2

Degradation of Selected Peptides by Atrial Peptide-Degrading Enzyme Preparation

| Peptide | % Degraded 1 h | % Degraded 2 h |
|---|---|---|
| API | 0 | 0 |
| APII (converted only to API) | 38 | 42 |
| AcAPII (converted only to AcAPI) | nd* | 88 |
| APIII (converted only to API) | 44 | 90 |
| ANF | >95 | nd |
| Leu—Tyr—Lys—Lys—Ile—Ile—Lys—Lys—Leu—Leu—Glu—Ser (PF-4 fragment) (SEQ ID NO: 5) | nd | 0 |
| Asn—Leu—Ala—Lys—Gly—Lys—Glu—Glu—Ser—Leu—Asp—Ser—Asp—Leu—Tyr—Ala—Glu—Leu—Arg (C-TAP 1-19) (SEQ ID NO: 6) | 48 | 66 |
| Asp—Val—Asn—Thr—Asp—Arg—Pro—Gly (Anxiety peptide) (SEQ ID NO: 7) | 4 | 6 |
| pGlu—Leu—Tyr—Glu—Asn—Lys—Pro—Arg—Arg—Pro—Tyr—Ile—Leu (Neurotensin) (SEQ ID NO: 8) | 12 | nd |
| pGlu—His—Trp—Ser—Tyr—Gly—Leu—Arg—Pro—Gly-$NH_2$ (LHRH) (SEQ ID NO: 9) | 0 | nd |

A series of small peptide fragments from the carboxy terminal side of the disulfide loop were then tested as substrates for ADE. Results are summarized in Table 3. As may be seen therein, none of these small peptides were readily cleaved by ADE.

TABLE 3

Degradation of Small Peptides by Atrial Peptide-degrading Enzyme Preparation

| Peptide | % Degraded |
|---|---|
| Asn—Ser—Phe—Arg—Tyr (SEQ ID NO: 10) | 8 |

TABLE 3-continued

Degradation of Small Peptides by
Atrial Peptide-degrading Enzyme Preparation

| Peptide | % Degraded |
|---|---|
| Asn—Ser—Phe—Arg (SEQ ID NO: 11) | 23 |
| Phe—Arg—Tyr | 17 |
| Ser—Phe—Arg—Tyr (SEQ ID NO: 12) | 12 |
| Boc—Asn—Ser—Phe—OCH$_3$ | 0 |
| Hip—Ser—Phe—Arg | 0 |

(e.) Enzyme Inhibitor Testing: To further characterize ADE, the extent of inhibition by several known peptidase inhibitors was determined. Results are summarized in Table 4. As may be deduced therefrom, ADE was greatly inhibited by reagents that bind irreversibly to thiols and by metal chelators. Thiol-reacting reagents, N-ethyl maleimide, and mercuri-compounds inhibited activity by almost 100%, while the chelator 1,10-phenanthroline inhibited activity to a slightly lesser extent. However, when the enzyme was dialyzed against 1 mM EDTA, activity was totally abolished, indicating that a tightly bound metal is required for enzymatic activity and can only be satisfactorily removed by dialysis. The enzyme was not inhibited by inhibitors of either serine proteases or acid proteases. Furthermore, it was not inhibited by the enkephalinase inhibitor phosphoramidon. The ACE inhibitor captopril resulted in-slight inhibition, as did the aldehyde-containing inhibitor leupeptin. It is not surprising that these two compounds inhibit to some extent, because captopril was made to inhibit a metal-containing enzyme and leupeptin is a good inhibitor of the cysteine peptidase papain. The fact that both thiol-reacting agents and metal chelators inhibit activity by greater than 70% suggests that ADE is a single enzyme containing both a tightly bound metal and an important thiol group rather than two separate enzymes.

TABLE 4

Percent Inhibition of ADE by General Peptidase Inhibitors

| Peptidase Class | Inhibitor | Conc. (mM) | Percent Inhibition |
|---|---|---|---|
| Cysteine | NEM | 5 | 97 |
|  | p-Chloromercuribenzoate | 1 | 95 |
|  | Hydroxymercuriphenyl sulfonic acid | 1 | 100 |
|  | E64 | 0.1 | 0 |
|  | Iodoacetamide | 1 | 10 |
|  | Iodoacetic acid | 1 | 0 |
| Metallo | EDTA | 5 | 20 |
|  | 1,10-Phenanthroline | 1 | 72 |
| Serine | PMSF | 1 | 8 |
| Serine & | Elastinal | 0.1 | 10 |
| Cysteine | Leupeptine | 0.1 | 33 |
|  | Chymostatin | 0.1 | 8 |
|  | Antipain | 0.1 | 0 |
| ACE | Captopril | 0.2 | 33 |
| Enkephalinase | Phosphoramidon | 0.001 | 0 |
| Acid | Pepstatin | 0.01 | 0 |

Both the molecular weight of ADE, as well as the inhibitor profile discussed above, suggest that this enzyme, found in the kidney, might be similar to an endopeptidase that cleaves ANF at the Ser-Phe residues, and which has been characterized in vascular smooth muscle and cultured endothelial cells (G. R. Johnson et al., *J. Biol. Chem.* 264:11637–11642 (1989); G. R. Johnson et al., *Biochem. Res. Commun.* 167:110–116 (1990)). Using gel filtration chromatography, a molecular weight of about 160,000 Daltons was found for ADE, slightly smaller than the 200,000 Dalton protein described by Johnson et al. (1990). Interestingly, both proteins are inhibited by metal chelators as well as by the thiol reagent NEM. This suggests that a crucial cysteine residue, as well as a chelated metal, is necessary for enzymatic activity.

Example 2

Synthesis and Testing of ADE Inhibitors (a.) Polypeptide Synthesis: The following general procedure was used for the syntheses of Ser-Leu-Arg-Arg-Ser-Ser-DAla-Gly-DAla-Asn-Ser-Phe-Arg-Tyr-NH$_2$ (I) (SEQ ID NO:2) Ser-Leu-Arg-Arg-Ser-Ser-DAla-Gly-DAla-Asn-Ser-DPhe-Arg-Tyr-NH$_2$ (II) (SEQ ID NO:2), Ser-Leu-Arg-Arg-Ser-Ser-DAla-Gly-DAla-Asn-DSer-Phe-Arg-Tyr-NH$_2$ (III) (SEQ ID NO:2), Ser-Leu-Arg-Arg-Ser-Ser-DAla-Gly-DAla-Asn-Cys-Phe-Arg-Tyr-NH$_2$ (IV) (SEQ ID NO:2), Ser-Leu-Arg-Arg-Ser-Ser-DAla-Gly-DAla-Asn-Cys-DPhe-Arg-Tyr-NH$_2$ (V) (SEQ ID NO:2), and Ser-Leu-Arg-Arg-Ser-Ser-DAla-Gly-DAla-Asn-Cys-DPhe-Arg-NH$_2$ (VI) (SEQ ID NO:2)

The peptides were synthesized by the solid-phase method on 1 g of p-methylbenzhydrylamine resin (0.6 mmol). Boc amino acid derivatives (1.5 mmol) and dicyclohexyl carbodiimide (1.5 mmol) were used for coupling. Benzyl and 2,6-dichlorobenzyl protection were respectively used for blocking side-chain hydroxy groups in serine and tyrosine. 4-Methylbenzyl and tosyl groups were respectively employed for the protection of the thiol function of cysteine and the guanidine function of arginine.

The couplings were monitored by the Kaiser ninhydrin test. In case a recoupling was necessary, 1-hydroxybenzotriazole (1.5 mmol) was added to catalyze the DCC coupling reaction. This latter procedure was also employed for coupling Boc-asparagine residues. Trifluoroacetic acid (TFA, 40% in CH$_2$Cl$_2$) with 10% indole or anisole as scavenger was the reagent for the removal of the Boc group. Neutralization of the TFA salt was achieved by diisopropyl ethyl amine (8% in CH$_2$Cl$_2$). The general synthesis cycle is shown in Table 5. The coupling time ranged from 1 to 18 h. After the synthesis, the peptide-resins were dried under vacuum.

Anhydrous hydrogen fluoride was used to cleave the peptide from the resin and achieve complete removal of all protecting groups. In a typical experiment, the peptide-resin was stirred with HF (10 mL/g of resin) at 0°–5° C. for 1 h in the presence of anisole (10%) and dimethyl sulfide (5%). After evaporation of HF in vacuo, the resin was washed with ether (3×30 mL) to remove organic impurities. The peptide was then extracted with acetic acid (1×5 mL) and water (5×10 mL). The solid crude peptide was obtained by lyophilization.

Purification of all the peptides was achieved on a Waters Delta prep 3000 HPLC instrument. A preparative reverse-phase (C-18) column (50×2.2 cm) containing Vydac 218TPB1015 was employed for the separation. A linear gradient of 120 min with a flow rate of 30 mL/min was found to be ideal for the purifications. A UV detector set at 223 or 224 nm was suitable for an attenuation value of 512. The purity of the peptides obtained after HPLC was greater than 99%. Table 6 shows the gradient used and the overall yields obtained for these peptides.

TABLE 5
SCHEDULE FOR SOLID-PHASE PEPTIDE SYNTHESIS (TFA DEPROTECTION-DCC COUPLING)

| Step | Reagent | Vol (mL) | Time (min) |
|---|---|---|---|
| 1 | DCM wash (3 times) | 15 | 5 |
| 2 | TFA-DCM-Indole | 15 | 1.5 |
| 3 | TFA-DCM-Indole | 15 | 30 |
| 4 | DCM wash (6 times) | 15 | 9 |
| 5 | DIEA-DCM | 15 | 1.5 |
| 6 | DIEA-DCM | 15 | 1.5 |
| 7 | DCM wash (6 times) | 15 | 9 |
| 8A | Boc-A.A in DCM (1.5 mmol) | 10 | 1.5 |
| 8B | DCC in DCM (1.0 M) | 1.5 | 120 or until monitoring shows complete reaction |
| 9 | Recouple if necessary by repeating steps 4-8 + HOBt (1.0 mmol) | | 160 |
| 10 | DCM wash (3 times) | 15 | 5 |

TABLE 6
PREPARATIVE HPLC DATA AND OVERALL YIELD

| Peptide | Gradient System Used | Overall Yield (%) |
|---|---|---|
| (I) | 4% CH$_3$CN (0.1% TFA)-16% CH$_3$CN (0.1% TFA) | 2.4 |
| (II) | 5% CH$_3$CN (0.1% TFA)-17% CH$_3$CN (0.1% TFA) | 56 |
| (III) | 5% CH$_3$CN (0.1% TFA)-18% CH$_3$CN (0.1% TFA) | 37.6 |
| (IV) | 8% CH$_3$CN (0.1% TFA)-20% CH$_3$CN (0.1% TFA) | 13.6 |
| (V) | 8% CH$_3$CN (0.1% TFA)-20% CH$_3$CN (0.1% TFA) | 42.3 |
| (VI) | 4% CH$_3$CN (0.1% TFA)-22% CH$_3$CN (0.1% TFA) | 6.0 |

Both gradient and isocratic analytical HPLC on a Vydac (TP21854) reverse-phase C-18 column were used to determine the purity and the chromatographic profile of the crude and pure peptides. A linear aqueous gradient of 5% CH$_3$CN (0.1% TFA)-50% CH$_3$CN (0.1% TFA) over a period of 30 min was suitable for these peptides. The UV detector was set at 220 nm with a flow rate of 1 mL/min. The retention times of each of the purified peptides is given in Table 7.

TABLE 7
GRADIENT ELUTION PROFILES

| Peptide | Retention Time (min) |
|---|---|
| (I) | 14.4 |
| (II) | 11.8 |
| (III) | 12.5 |
| (IV) | 13.9 |
| (V) | 13.5 |
| (VI) | 11.5 |

The retention times by isocratic elution are shown in Table 8.

TABLE 8
ISOCRATIC ELUTION PROFILE

| Peptide | Solvent System in H$_2$O | Retention Time (min) | k' |
|---|---|---|---|
| (I) | 16% CH$_3$CN (0.1% TFA) | 11.2 | 2.7 |
| (II) | 15% CH$_3$CH (0.1% TFA) | 6 | 1.94 |
| (III) | 16% CH$_3$CN (0.1% TFA) | 6.1 | 1.97 |
| (IV) | 18% CH$_3$CN (0.1% TFA) | 7.4 | 2.3 |
| (V) | 18% CH$_3$CN (0.1% TFA) | 6.6 | 2.13 |
| (VI) | 17% CH$_3$CN (0.1% TFA) | 5.7 | 0.91 |

The amino acid analysis results (obtained from the University of California, Davis, Calif.) were found to be in accord with expected values. These are reported in Table 9.

TABLE 9
AMINO ACID ANALYSIS RESULTS[a]

| Peptide | Asn | Ser | Gly | Ala | Leu | Tyr | Phe | Arg | Cys |
|---|---|---|---|---|---|---|---|---|---|
| (I) | 1.01 (1) | 3.3 (4) | 0.98 (1) | 1.91 (2) | 0.94 (1) | 1.01 (1) | 0.95 (1) | 3.11 (3) | |
| (II) | 0.99 (1) | 3.4 (4) | 0.97 (1) | 2.04 (2) | 1.0 (1) | 1.0 (1) | 0.98 (1) | 3.0 (3) | |
| (III) | 1.01 (1) | 3.49 (4) | 0.96 (1) | 1.9 (2) | 1.03 (1) | 1.03 (1) | 1.01 (1) | 3.05 (3) | |
| (IV) | 0.99 (1) | 2.58 (3) | 0.91 (1) | 2.03 (2) | 1.0 (1) | 1.0 (1) | 0.97 (1) | 3.09 (3) | 0.96 (1) |
| (V) | 1.01 (1) | 2.6 (3) | 0.95 (1) | 1.88 (2) | 1.01 (1) | 1.01 (1) | 0.99 (1) | 3.14 (3) | 1.08 (1) |
| (VI) | 1.03 (1) | 2.55 (3) | 1.00 (1) | 1.87 (2) | 1.00 (1) | — | 1.00 (1) | 3.22 (3) | 0.97 (1) |

[a]The expected amino acid amounts are given in parentheses.

(b.) HPLC Enzyme Assay: In this experiment, a 1.5 ml aliquot of the pooled active fractions from the hydroxylapatite column was injected onto the Dynamax column and eluted at 1.0 ml/min with a 10- to 300-mm KPO$_4$ gradient. A 20-µL sample of each fraction was incubated with 10 µL of AcAPII (6 µg) and 20 µL H$_2$O, for a final volume of 50 µL. The incubation lasted 1 h at 37° C., at which time the samples were boiled to stop the reaction and centrifuged. A 15-µL sample of the supernatant was then injected onto a Vydac TP21854 reverse-phase column (4.6×250 mm) and eluted with 22% CH$_3$CN, 0.01% TFA in H$_2$O.

As determined by a review of the HPLC tracings which were obtained, the earlier eluting fractions did not cleave AcAPII, the starting material (retention time 10.88 min) and the internal standard (retention time 8.14 min) being the only peaks visible. At approximately fraction. #11, a peak representing AcAPI was visible at a retention time of 6.08 min. In the ensuing fractions, the amount of AcAPI produced increased, and AcAPII decreased. The conversion appeared to be quantitative, with no further degradation of AcAPI apparent. In later fractions, the amount of AcAPI produced decreased, indicating that the peak of activity was ending. In this particular run, fractions #12 through 17 were pooled.

(c.) ADE inhibition by Compounds (I)–(VI): The extent of inhibition of ADE activity by compounds (I) through (VI) was evaluated as described for known peptidase inhibitors in Example 1, part (e). As may be seen in Table 10, all of the novel compounds were found to be moderate to superior inhibitors of ADE activity.

TABLE 10
SAR of Tetradecapeptide ADE Inhibitors
SerLeuArgArgSerSerDAlaGlyDAlaAsn-R

| | R | % Inhibition At 0.1 mM | IC$_{50}$ (µM) |
|---|---|---|---|
| (I) | —Ser—Phe—Arg—Tyr—NH$_2$ | 46 | |

TABLE 10-continued

SAR of Tetradecapeptide ADE Inhibitors
SerLeuArgArgSerSerDAlaGlyDAlaAsn-R

| R | | % Inhibition At 0.1 mM | IC$_{50}$ ($\mu$M) |
|---|---|---|---|
| | (SEQ ID NO: 12) | | |
| (II) | —Ser—DPhe—Arg—Tyr—NH$_2$ | 28 | |
| | (SEQ ID NO: 12) | | |
| (III) | —DSer—Phe—Arg—Tyr—NH$_2$ | 22 | |
| | (SEQ ID NO: 12) | | |
| (IV) | —Cys—Phe—Arg—Tyr—NH$_2$ | 68 | 32.5 |
| | (SEQ ID NO: 13) | | |
| (V) | —Cys—DPhe—Arg—Tyr—NH$_2$ | 81 | 14.5 |
| | (SEQ ID NO: 13) | | |
| (VI) | —Cys—DPhe—Arg—NH$_2$ | 74 | |

EXAMPLE 3

Blood Pressure Measurements in Spontaneously Hypertensive Rats

This experiment was carried out to evaluate the effects of an ADE inhibitor compound of the invention upon blood pressure (systolic and diastolic) and heart rate in spontaneously hypertensive rats ("SHR"). Twenty-eight male SHR, weighing 200–300 g at the initiation of study, having a systolic blood pressure of 160 mm Hg or higher, and obtained from Charles River Laboratories (Wilmington, Mass.), were tested over a nine-day period. The animal room environment and photoperiod were controlled (temperature approximately 22° C.±3° C., humidity of 40 to 70%, 12 h light, 12 h dark), as was diet.

The compounds to be administered (compound (V), above, and rat ANF ("rANF")) were dissolved in a 0.9% saline solution and administered intravenously. The test animals were divided into seven distinct groups for purposes of dose administration, as follows:

Group 1. Four SHR rats were infused with 100 pmole/minute of RANF (0.026 ml/minute) for 20 minutes.

Group 2. Four SHR rats were administered an i.v. bolus of 2 mg/kg of compound (V).

Group 3. Four SHR rats were administered an i.v. bolus of 10 mg/kg of compound (V).

Group 4. Four SHR rats were infused with 0.2 mg/kg/min of compound (V) (0.026 ml/minute) for 20 minutes.

Group 5. Four SHR rats were administered an i.v. bolus of 2 mg/kg of compound (V) and then infused with 100 pmole/minute of RANF (0.026 ml/minute for 20 minutes.

Group 6. Four SHR rats were administered an i.v. bolus of 10 mg/kg of compound (V) and then infused with 100 pmole/minute of RANF (0.026 ml/minute) for 20 minutes.

Group 7. Four SHR rats were infused with 0.2 mg/kg/min of compound (V) (0.026 ml/minute) for 20 minutes and then infused with 100 pmole/minute of RANF (0.26 ml/minute) for 20 minutes.

Blood pressure and heart rate determinations were made at 5 minute intervals for 20 minutes prior to dose and at 5 minute intervals for a minimum of 40 minutes following the initiation of test article administration or until a return to control values was realized. Blood pressure was measured continuously for one minute using a Statham P23Db pressure transducer (Statham Instruments, Hata Rey, Puerto Rico), and a Grass Model 7 Polygraph (Glass Instrument Company, Quincy, Mass.). Heart rate was measured using a Narco biotachometer BT-1200 (Narco Biosystems, Houston, Tex.).

As presented in Tables 11 and 12, the intravenous infusion of RANF alone at 100 pmole/minute for 20 minutes produced decreases in both systolic and diastolic blood pressure. This effect persisted throughout 20 minutes following the discontinuation of the infusion. No effects upon heart rate were observed. Dose-related decreases in systolic and diastolic blood pressure were observed following bolus injections of (V) at 2 and 10 mg/kg. The duration of the blood pressure lowering persisted through 20 minutes following the administration of (V) at 2 mg/kg and through 35 minutes following the dose of (V) at 10 mg/kg. No effects upon heart rate were observed. The intravenous infusion of (V) alone at 0.2 mg/kg/minute for 20 minutes produced minimal decreases in systolic and diastolic blood pressure. This effect was observed primarily during the infusion and persisted for 10 minutes following the conclusion of the dose. No effects upon heart rate were observed. Combination dosing of (V) at 2 mg/kg by bolus injection immediately followed by a 20 minute infusion of rANF at 100 pmole/minute produced decreases in systolic and diastolic blood pressure. These decreases in blood pressure were greater than those decreases observed with the RANF or compound (V) alone. However, the duration of effect remained the same. The simultaneous administration of (V) at 10 mg/kg by bolus injection and a 20 minute infusion of RANF at 100 pmole/minute produced maximum decreases in systolic and diastolic blood pressure. These decreases were of greater magnitude and duration than those decreases observed with the RANF or compound (V) alone. A decrease in heart rate was also observed. The infusion of (V) at 0.2 mg/kg/minute for 20 minutes immediately followed by a 20 minute infusion of rANF at 100 pmole/minute produced decreases in blood pressure (systolic and diastolic) that were comparable to those decreases observed with the compound (V) or rANF alone. No consistent effects upon heart rate were observed.

TABLE 11

The Effects of Intravenously Administered rANF and (V)
Upon Systolic Blood Pressure in Spontaneously Hypertensive Rats
Mean Change From Control (N = 4)

| Test Article | Dose | Interval/minute | | | | | | | | | | | |
|---|---|---|---|---|---|---|---|---|---|---|---|---|---|
| | | 0 | 5 | 10 | 15 | 20 | 25 | 30 | 35 | 40 | 45 | 50 | 55 | 60 |
| rANF, 20 min. infusion | 100 pmole/min. | −3$^a$ | −23 | −50 | −43 | −38$^b$ | −29 | −20 | −10 | +3 | — | — | — | — |
| (V), bolus injection | 2 mg/kg | −80 | −50 | −30 | −14 | −13 | −4 | +1 | +2 | +4 | — | — | — | — |
| (V), bolus injection | 10 mg/kg | −76 | −119 | −100 | −84 | −55 | −41 | −29 | −21 | +9 | — | — | — | — |
| (V), 20 min. infusion | 0.2 mg/kg/min. | −1 | −10 | −18 | −16 | −26 | −16 | −9 | 0 | +5 | — | — | — | — |
| (V), bolus injection plus rANF, 20 min. infusion | 2/mg/kg 100 pmole/min. | −97 | −72 | −66 | −55 | −60 | −32 | −27 | −20 | −5 | — | — | — | — |

TABLE 11-continued

The Effects of Intravenously Administered rANF and (V)
Upon Systolic Blood Pressure in Spontaneously Hypertensive Rats
Mean Change From Control (N = 4)

| | | | | | | | | | | | | | | |
|---|---|---|---|---|---|---|---|---|---|---|---|---|---|---|
| (V), bolus injection plus | 10 mg/kg | −91 | −131 | −120 | −103 | −95 | −89 | −85 | −79 | −70 | −65 | −63 | −60 | −58 |
| rANF, 20 min. infusion | 100 pmole/min. | | | | | | | | | | | | | |
| (V), 20 min. infusion plus | 0.2 mg/kg/min. | −11 | −11 | −16 | −16[c] | −25 | −22 | −32 | −41 | −37[d] | −28 | −27 | −25 | −17 |
| rANF, 20 min. infusion | 100 pmole/min. | | | | | | | | | | | | | |

| | | Interval/minute | | | | | | | | | | | |
|---|---|---|---|---|---|---|---|---|---|---|---|---|---|
| Test Article | Dose | 65 | 70 | 75 | 80 | 85 | 90 | 95 | 100 | 105 | 110 | 115 | 120 | 125 |
| rANF, 20 min. infusion | 100 pmole/min. | — | — | — | — | — | — | — | — | — | — | — | — | — |
| (V), bolus injection | 2 mg/kg | — | — | — | — | — | — | — | — | — | — | — | — | — |
| (V), bolus injection | 10 mg/kg | — | — | — | — | — | — | — | — | — | — | — | — | — |
| (V), 20 min. infusion | 0.2 mg/kg/min. | — | — | — | — | — | — | — | — | — | — | — | — | — |
| (V), bolus injection plus | 2/mg/kg | — | — | — | — | — | — | — | — | — | — | — | — | — |
| rANF, 20 min. infusion | 100 pmole/min. | | | | | | | | | | | | | |
| (V), bolus injection plus | 10 mg/kg | −51 | −43 | −38 | −35 | −35 | −28 | −24 | −19 | −14 | −10 | −8 | −4 | +2 |
| rANF, 20 min. infusion | 100 pmole/min. | | | | | | | | | | | | | |
| (V), 20 min. infusion plus | 0.2 mg/kg/min. | −12 | −6 | −3 | +3 | — | — | — | — | — | — | — | — | — |
| rANF, 20 min. infusion | 100 pmole/min. | | | | | | | | | | | | | |

[a] infusions initiated or bolus injection administered at time interval 0
[b] single infusions concluded at time interval 20
[c] secondary infusion rANF initiated
[d] secondary infusion rANF terminated

TABLE 12

The Effects of Intravenously Administered rANF and (V)
Upon Diastolic Blood Pressure in Spontaneously Hypertensive Rats
Mean Change From Control (N = 4)

| | | Interval/minute | | | | | | | | | | | |
|---|---|---|---|---|---|---|---|---|---|---|---|---|---|
| Test Article | Dose | 0 | 5 | 10 | 15 | 20 | 25 | 30 | 35 | 40 | 45 | 50 | 55 | 60 |
| rANF, 20 min. infusion | 100 pmole/min. | 0[a] | −14 | −17 | −24 | −19[b] | −14 | −8 | −3 | +3 | — | — | — | — |
| (V), bolus injection | 2 mg/kg | −61 | −40 | −14 | −8 | −10 | +1 | +5 | +7 | 0 | — | — | — | — |
| (V), bolus injection | 10 mg/kg | −66 | −76 | −61 | −55 | −35 | −27 | −17 | −15 | +10 | — | — | — | — |
| (V), 20 min. infusion | 0.2 mg/kg/min. | −4 | −12 | −15 | −18 | −20 | −13 | −14 | 0 | −2 | — | — | — | — |
| (V), bolus injection plus | 2/mg/kg | −71 | −50 | −43 | −34 | −38 | −24 | −25 | −16 | −9 | — | — | — | — |
| rANF, 20 min. infusion | 100 pmole/min. | | | | | | | | | | | | | |
| (V), bolus injection plus | 10 mg/kg | −64 | −79 | −66 | −54 | −49 | −44 | −42 | −39 | −35 | −31 | −21 | −31 | −30 |
| rANF, 20 min. infusion | 100 pmole/min. | | | | | | | | | | | | | |
| (V), 20 min. infusion plus | 0.2 mg/kg/min. | −4 | 0 | −13 | −10 | −15[c] | −13 | −18 | −23 | −15[d] | −13 | −13 | −13 | −3 |
| rANF, 20 min. infusion | 100 pmole/min. | | | | | | | | | | | | | |

| | | Interval/minute | | | | | | | | | | | |
|---|---|---|---|---|---|---|---|---|---|---|---|---|---|
| Test Article | Dose | 65 | 70 | 75 | 80 | 85 | 90 | 95 | 100 | 105 | 110 | 115 | 120 | 125 |
| rANF, 20 min. infusion | 100 pmole/min. | — | — | — | — | — | — | — | — | — | — | — | — | — |
| (V), bolus injection | 2 mg/kg | — | — | — | — | — | — | — | — | — | — | — | — | — |
| (V), bolus injection | 10 mg/kg | — | — | — | — | — | — | — | — | — | — | — | — | — |
| (V), 20 min. infusion | 0.2 mg/kg/min. | — | — | — | — | — | — | — | — | — | — | — | — | — |
| (V), bolus injection plus | 2/mg/kg | — | — | — | — | — | — | — | — | — | — | — | — | — |
| rANF, 20 min. infusion | 100 pmole/min. | | | | | | | | | | | | | |
| (V), bolus injection plus | 10 mg/kg | −26 | −22 | −17 | −16 | −15 | −6 | −4 | 0 | +3 | +3 | +4 | +8 | +15 |
| rANF, 20 min. infusion | 100 pmole/min. | | | | | | | | | | | | | |
| (V), 20 min. infusion plus | 0.2 mg/kg/min. | −3 | −3 | +7 | +7 | — | — | — | — | — | — | — | — | — |
| rANF, 20 min. infusion | 100 pmole/min. | | | | | | | | | | | | | |

[a] infusions initiated or bolus injection administered at time interval 0
[b] single infusions concluded at time interval 20
[c] secondary infusion rANF initiated
[d] secondary infusion rANF terminated

We claim

1. A peptide selected from the group consisting of the following sequences (I), (II), (III), (IV), (V) and (VI):
(I) Ser-Leu-Arg-Arg-Ser-Ser-DAla-Gly-DAla-Asn-Ser-Phe-Arg-Tyr-$NH_2$ (SEQ ID NO:2);
(II) Ser-Leu-Arg-Arg-Ser-Ser-DAla-Gly-DAla-Asn-Ser-DPhe-Arg-Tyr-$NH_2$ (SEQ ID NO:2);
(III) Ser-Leu-Arg-Arg-Ser-Ser-DAla-Gly-DAla-Asn-DSer-Phe-Arg-Tyr-$NH_2$ (SEQ ID NO:2);
(IV) Ser-Leu-Arg-Arg-Ser-Ser-DAla-Gly-DAla-Asn-Cys-Phe-Arg-Tyr-$NH_2$ (SEQ ID NO:3);
(V) Ser-Leu-Arg-Arg-Ser-Ser-DAla-Gly-DAla-Asn-Cys-DPhe-Arg-Tyr-$NH_2$ (SEQ ID NO:3);
(VI) Ser-Leu-Arg-Arg-Ser-Ser-DAla-Gly-DAla-Asn-Cys-DPhe-Arg-$NH_2$ (SEQ ID NO:4).

2. The peptide of claim 1 consisting of the amino acid sequence (I).

3. The peptide of claim 1 consisting of the amino acid sequence (II).

4. The peptide of claim 1 consisting of the amino acid sequence (III).

5. The peptide of claim 1 consisting of the amino acid sequence (IV).

* * * * *